US00PP23734P2

(12) United States Plant Patent
Verschoor

(10) Patent No.: US PP23,734 P2
(45) Date of Patent: Jul. 9, 2013

(54) ***PHLOX* PLANT NAMED 'TWISTER'**

(50) Latin Name: *Phlox paniculata*
Varietal Denomination: 'Twister'

(76) Inventor: Jan Verschoor, Haarlem (NL)

( * ) Notice: Subject to any disclaimer, the term of this patent is extended or adjusted under 35 U.S.C. 154(b) by 239 days.

(21) Appl. No.: 13/134,015

(22) Filed: May 26, 2011

(51) Int. Cl.
*A01H 5/00* (2006.01)

(52) U.S. Cl.
USPC ..... Plt./320

(58) Field of Classification Search
USPC ..... Plt./320
See application file for complete search history.

*Primary Examiner* — June Hwu
*Assistant Examiner* — Louanne Krawczewicz Myers
(74) *Attorney, Agent, or Firm* — Audrey Charles

(57) ABSTRACT

A new and distinct cultivar of *Phlox* plant named 'Twister', particularly distinguished by red-purple and white bicolored flowers, compact habit, healthy foliage, and good mildew resistance with good garden performance, is disclosed.

1 Drawing Sheet

Latin name of genus and species of plant claimed: *Phlox paniculata.*

Variety denomination: 'Twister'.

BACKGROUND OF THE INVENTION

The present invention relates to a new and distinct cultivar of *Phlox* plant botanically known as *Phlox paniculata* and hereinafter referred to by the cultivar name 'Twister'. The new cultivar originated as a naturally-occurring whole plant mutation in a population of *Phlox* 'Peppermint Twist', U.S. Plant Pat. No. 18,196. The new cultivar was discovered and selected in 2007 in an outdoor nursery location in Haarlem, The Netherlands.

Asexual reproduction of the new *Phlox* by vegetative cuttings in a controlled environment in Haarlem, The Netherlands since the summer of 2008, has shown that the unique features of the *Phlox* are stable and reproduced true to type in successive generations.

SUMMARY OF THE INVENTION

The following are the most outstanding and distinguishing characteristics of this new cultivar when grown under normal horticultural practices in Haarlem, The Netherlands:

1. Red-purple and white bicolored flowers;
2. Compact habit;
3. Healthy foliage; and
4. Good mildew resistance with good garden performance.

Of the many commercially available *Phlox* cultivars, the most similar in comparison to the new cultivar is the parent 'Peppermint Twist', U.S. Plant Pat. No. 18,196. However, in side by side comparisons in Haarlem, The Netherlands, plants of the new cultivar 'Twister' differ from plants of 'Peppermint Twist' by having a different flower color pattern.

In addition the new cultivar can be compared to the commercially available cultivar 'Starfire', not patented. However, in side by side comparisons in Haarlem, The Netherlands, plants of the new cultivar 'Twister' differ from plants of 'Starfire' in at least the following characteristics:

1. Plants of the new cultivar have a flower color that is more intense than plants of 'Starfire';

2. Plants of the new cultivar are more compact, as measured by plant height, than plants of 'Starfire'; and
3. Plants of the new cultivar have thicker stems making for a sturdier plant than plants of 'Starfire'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Twister'. The plant was field grown for approximately 2 years in Haarlem, The Netherlands in an outdoor nursery location. The plant was transplanted into a container for photography purposes.

DETAILED BOTANICAL DESCRIPTION

Figure 1:
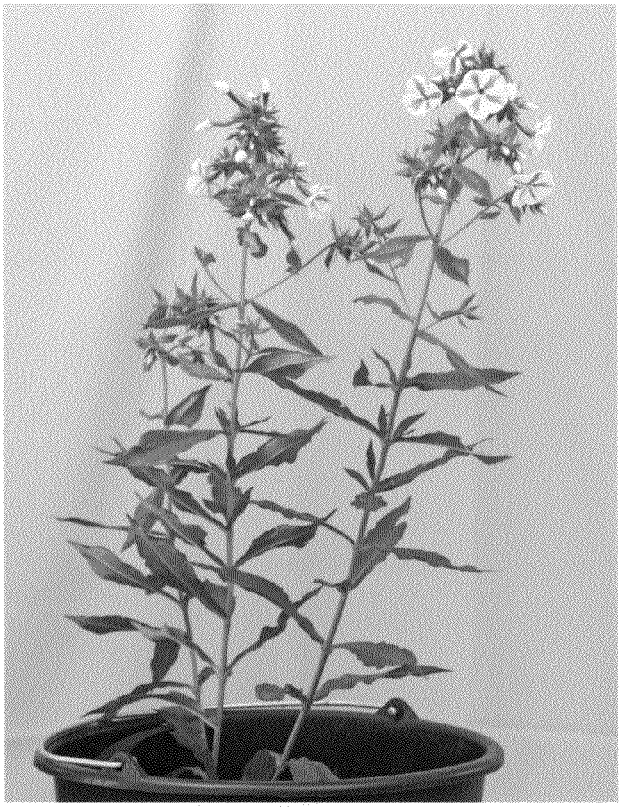
FIG. 1 illustrates a side view of the overall growth and flowering habit of 'Twister'.
Figure 2:
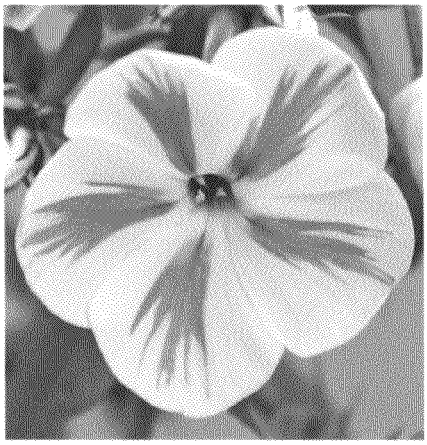
FIG. 2 illustrates a close-up view of an individual inflorescence of 'Twister'.
Figure 3:
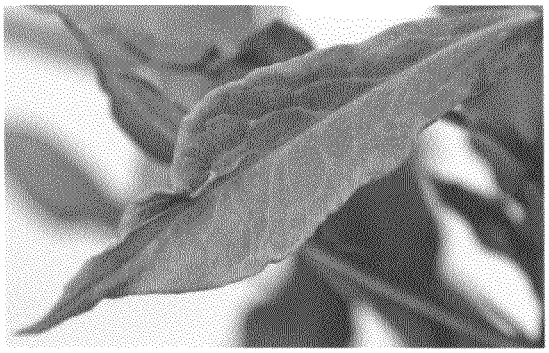
FIG. 3 illustrates a close-up view of the foliage of 'Twister'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2007 edition, except where general color terms of ordinary significance are used. The data which define these characteristics were collected from asexual reproductions carried out in Haarlem, The Netherlands. The plant history was taken in April 2011 on 2-year-old field grown plants which were planted and grown outdoors in daytime temperatures between 14° C. and 28° C. and nighttime temperatures between 5° C. and 18° C. No pinching, growth retardants or photoperiodic treatments were used. Observations were made when the plants were in natural daylight conditions.

Botanical classification: *Phlox paniculata* cultivar 'Twister'.

Parentage:

*Parent*.—'Peppermint Twist', U.S. Plant Pat. No. 18,196.

Propagation:

*Type cutting*.—Vegetative cutting.

*Time to produce a rooted cutting*.—Approximately 30 days with average soil temperature of 21° C.

*Root description*.—White, thin, fibrous, sparse.

*Rooting habit*.—Freely branching.

Plant description:

*Type*.—Herbaceous perennial. Overall shape: Narrow inverted triangle. High temperature tolerance: Tolerant to at least 35° C. Low temperature tolerance: Hardy to at least USDA Zone 4. Excellent garden performance.

*Commercial crop time*.—Approximately 25 weeks from rooted cutting to finish in a 1.5 liter container.

*Growth habit and general appearance*.—Upright, moderately vigorous.

*Size*.—Height from soil level to top of plant plane: Approximately 55.2 cm. Width: Approximately 33.1 cm. Rate of growth: In spring, approximately 10 cm per month.

*Branching habit*.—Low to moderate basal branching; pinching will improve basal branching; flowering stems grow from base. Quantity of branches per plant: Approximately 3 flowering stems.

*Stem*.—Shape: Rounded. Strength: Strong. Aspect: Erect. Length to base of inflorescence: Approximately 38.0 cm. Diameter: Approximately 4.0 mm. Length of central internode: Approximately 3.1 cm. Texture: Glabrous, slightly glossy. Color of young and mature stems: 144A.

Foliage description:

*General description*.—Quantity of leaves per stem: Approximately 24. Form: Simple. Arrangement: Opposite. Durability to stress: High.

*Leaves*.—Shape: Narrowly elliptic to narrowly obovate. Margin: Irregularly crenate. Apex: Narrowly acute. Base: Truncate. Venation pattern: Pinnate. Length of mature leaf: Approximately 9.9 cm. Width of mature leaf: Approximately 2.3 cm. Texture of upper and lower surfaces: Smooth, glabrous. Color of upper surface of young foliage: 144A with venation of 144B. Color of lower surface of young foliage: 143C with venation of 144C to 144D. Color of upper surface of mature foliage: N137B to N137C with venation of 144B. Color of lower surface of mature foliage: 147B with venation of 144C to 144D.

*Petiole*.—Shape: V-shaped. Length: Approximately 2.0 mm. Width: Approximately 3.0 mm. Height: Approximately 2.0 mm. Color: 144C.

Flowering description:

*Flowering habit*.—Freely flowering under outdoor growing conditions with substantially continuous blooming from summer through late summer.

*Lastingness of flower on the plant*.—Approximately 10 days.

*Flowering response time*.—Approximately 60 days.

Inflorescence description:

*General description*.—Type: Compound terminal panicle, self-cleaning. Fragrance: Moderately, sweet and pleasant; typical Phlox paniculata scent. Height: Approximately 15.1 cm. Width: Approximately 13.1 cm. Quantity of opened flowers per inflorescence: Approximately 10. Rate of flower opening: Approximately 20% of the flowers at any stage.

*Peduncle*.—Strength: Strong. Aspect: Erect primary peduncles with secondary peduncles at approximately a 45° angle. Length of primary: Approximately 15.4 cm. Diameter of primary: Approximately 2.0 mm. Length of secondary: Approximately 6.3 cm. Diameter of secondary: Approximately 1.0 mm. Texture: Smooth, glabrous. Color: 144B to 144C, occasionally with overlay of 182A.

Flower description:

*General description*.—Type: Single. Shape: Salverform. Aspect: Upright and outward.

*Bud just before opening*.—Quantity per inflorescence: Approximately 140. Shape: Elliptic to oblanceolate. Length: Approximately 1.6 cm. Diameter: Approximately 5.0 mm. Color: Petals of 155C with 157D; calyx 147B to 147C with lighter margins of 145C to 145D. Rate of opening: Approximately 4 days.

*Corolla*.—Depth: Approximately 2.3 cm. Diameter: Approximately 3.2 cm.

*Petals*.—Quantity: 5 occasionally 6, lower 60% of each petal fused into a narrow tube. Arrangement: Rotate. Appearance: Dull. Shape, lobe: Spathulate. Margin: Entire. Apex: Rounded. Length: Approximately 3.4 cm, lower 2.0 cm fused into tube. Length of free portion: Approximately 1.4 cm. Width: Approximately 1.6 cm. Texture of upper and lower surfaces: Smooth. Color of upper surface when first open: NN155C to NN155D with a central irregular stripe of N57A to N57B with 58B, inner surface of tube 72A to 72B. Color of lower surface when first open: NN155B with a central irregular stripe of 61D, outer surface of tube 77B. Color of upper surface when fully open: NN155B to NN155C with a central irregular stripe of 61D, inner surface of tube 72A to 72B. Color of lower surface when fully open: NN155B with a central irregular stripe of 62A to 62B, outer surface of tube 77B.

*Calyx*.—Shape: Campanulate. Length: Approximately 9.5 mm. Diameter: Approximately 4.5 mm.

*Sepals*.—Quantity: 5, lower 15% fused into a narrow tube. Arrangement: In a single whorl. Appearance: Moderately glossy. Shape: Linear. Margin: Entire. Apex: Narrow apiculate. Length: Approximately 9.5 mm. Width: Approximately 2.0 mm. Texture of upper and lower surfaces: Smooth, moderately glossy. Color of upper and lower surfaces of immature sepals: 147B to 147C with margins of 145C to 145D. Color of upper and lower surfaces of mature sepals: 147B to 147C with margins of 145C to 145D.

*Pedicel*.—Strength: Strong. Aspect: Erect when directly adjoining peduncle, others at an approximately 60° angle. Length: Approximately 4.0 mm. Diameter: Approximately 1.0 mm. Texture: Smooth, glabrous. Color: 144B to 144C.

*Reproductive organs*.—Androecium: Stamen quantity: 5 per flower, basifixed. Anther shape: Oblong. Anther length: Approximately 2.0 mm. Filament length: Approximately 0.5 mm. Anther color: 160D. Pollen amount: Sparse. Pollen color: 11D. Gynoecium: Pistil quantity: 1 per flower. Pistil length: Approximately 1.6 cm. Stigma shape: Cleft (3-parted). Stigma color: 150D. Style length: Approximately 1.5 cm. Style color: 145C. Ovary color: 143A.

Seed and fruit production: Neither seed nor fruit production has been observed.

Disease and pest resistance: Good mildew resistance. No particular resistance or susceptibility to other diseases or insects noted to date.

What is claimed is:

1. A new and distinct cultivar of *Phlox* plant named 'Twister', substantially as herein shown and described.

* * * * *